(12) United States Patent
Edwards et al.

(10) Patent No.: US 8,033,724 B2
(45) Date of Patent: Oct. 11, 2011

(54) RAPID ASSEMBLY AND OPERATION OF AN X-RAY IMAGING SYSTEM

(75) Inventors: William Talion Edwards, Foristell, MO (US); Morteza Safai, Seattle, WA (US); Gary E. Georgeson, Federal Way, WA (US); Daniel Shedlock, Knoxville, TN (US)

(73) Assignee: The Boeing Company, Chicago, IL (US)

( * ) Notice: Subject to any disclaimer, the term of this patent is extended or adjusted under 35 U.S.C. 154(b) by 115 days.

(21) Appl. No.: 12/495,224

(22) Filed: Jun. 30, 2009

(65) Prior Publication Data

US 2010/0327174 A1    Dec. 30, 2010

(51) Int. Cl.
*H05G 1/06* (2006.01)
*G01N 23/203* (2006.01)

(52) U.S. Cl. ............ 378/194; 378/58; 378/87; 378/102; 378/146; 378/198

(58) Field of Classification Search .................... 378/58, 378/87, 102, 146, 194, 198
See application file for complete search history.

(56) References Cited

U.S. PATENT DOCUMENTS

| | | | |
|---|---|---|---|
| 3,737,661 A | 6/1973 | Applegate | |
| 4,277,685 A * | 7/1981 | Covic et al. | 378/7 |
| 4,397,032 A * | 8/1983 | Kuipers | 378/11 |
| 4,516,256 A * | 5/1985 | Wapperom | 378/60 |
| 5,450,466 A * | 9/1995 | Kadowaki et al. | 378/194 |
| 5,483,957 A * | 1/1996 | Janssen et al. | 378/194 |
| 5,499,284 A | 3/1996 | Pellegrino | |
| 5,666,393 A | 9/1997 | Annis | |
| 5,680,436 A | 10/1997 | Nyzen | |
| 6,292,533 B1 | 9/2001 | Swift et al. | |
| 6,314,157 B1 * | 11/2001 | Tachizaki | 378/4 |
| 7,463,714 B2 | 12/2008 | Edwards et al. | |
| 7,505,556 B2 | 3/2009 | Chalmers et al. | |
| 7,508,910 B2 * | 3/2009 | Safai et al. | 378/57 |
| 7,529,343 B2 | 5/2009 | Safai et al. | |

OTHER PUBLICATIONS

PCT Invitation to Pay Addtional Fees and, Where Applicable, Protect Fee for Application No. PCT/US2010/035909, dated Nov. 9, 2010, 6 pgs.
Addicott, "Characterization and Optimization of Radiography by Selective Detection Backscatter X-Ray Imaging Modality", MS Thesis of Nuclear and Radiological Engineering, University of Florida, 2006, 242 pgs.
Allard et al, "Image Processing Techniques for Lateral Migration Radiography Land Mine Images," Technical Report, ARO Grant No. DAAG-55-98-1-0400, University of Florida, Jun. 2000, 80 pgs.
Braith et al., "TPS NDE Backscatter X-Ray Support Tooling Gimbal Assembly" drawings, Jan. 2006, obtained from NucSafe, Inc. engineer, 1 pg.

(Continued)

*Primary Examiner* — Edward Glick
*Assistant Examiner* — Thomas R Artman
(74) *Attorney, Agent, or Firm* — Caven & Aghevli LLC

(57) ABSTRACT

Methods and systems for X-ray imaging are disclosed. An X-ray imaging system includes an X-ray tube to generate X-rays and a detector array to capture scattered X-rays. A rotational collimator directs the X-rays at an object under inspection. Rotational mechanisms rotate the X-ray tube and the detector array about a roll axis and a yaw axis to inspect various portions of the object. A track unit mechanism moves the X-ray imaging system linearly along a track unit to further inspect portions of the object.

19 Claims, 6 Drawing Sheets

OTHER PUBLICATIONS

Dugan et al, "Detection of Land Mines Using Lateral Migration X-ray Radiography," Proc SPIE 48th Annual Meeting, Symposium on Optical Science and Technology, Penetrating Radiation Systems and Applications V, vol. 5199, San Diego, Aug. 2003, 12 pgs.

Dugan et al, "Development and Field Testing of a Mobile Backscatter X-ray Lateral Migration Radiography Land Mine Detection System," SPIE Proc on Detection and Remediation Technologies for Mines And Minelike Targets VII, vol. 4742, Orlando, FL, Apr. 2002, pp. 120-131.

Dugan et al., "Lateral Migration Radiography Image Signatures for the Detection and Indentification of Buried Land Mines", Grant Extension Technical Report, Univ of Florida, Jan. 2002, 24 pgs.

Dugan et al, "Lateral Migration Radiography Image Signatures for the Detection and Identification of Buried Land Mines," Final Technical Report, ARO Grant DAAG-55-98-1-0400, University of Florida, Aug. 2001, 152 pgs.

Dugan et al,"Status of the XMIS X-ray Backscatter Radiography Land Mine Detection System," SPIE Proceedings on Detection And Remediation Technologies for Mines and Mine like Targets VIII, vol. 5089, Orlando, Apr. 2003, 12 pgs.

Jacobs et al, "Detection/Identification of Land Mines by Lateral Migration Radiography," Proc Second International Conference on the Detection of Abandoned Mines, Institution of Electrical Engineers Publication No. 458, Edinburg, UK, Oct. 1998., pp. 152-156.

Jacobs, "Imaging Subsurface Defects Using X-Ray Lateral Migration Radiography / A New Backscatter Technique," Proceedings of ASNT Conference on Real-Time Radioscopy and Digital Imaging, Aug. 1999, 7 pgs.

Keshavmurthy et al, "Analytical Studies of a Backscatter X-ray Imaging Landmine Detection System," SPIE Proceedings on Detection and Remediation Technologies for Mine and Mine like Targets, vol. 2765-52, pp. 512-525, Apr. 1996.

Neer et al., "Gimbal Assembly" drawings, Oct. 2003, 1 of 2, obtained from NucSafe, Inc. engineer, 1 pg.

Neer et al., "Gimbal Assembly" drawings, Oct. 2003, 2 of 2, obtained from NucSafe, Inc. engineer, 1 pg.

Shedlock et al, "Optimization of a RSD X-Ray Backscatter System for Detecting Defects in the Space Shuttle External Tank Thermal Foam Insulation," Proc SPIE 50th Annual Meeting, Symposium on Optical Science and Technology, Penetrating Radiation Systems And Applications, San Diego, Aug. 2005, 12 pgs.

Shedlock et al, "Preliminary Measurements Supporting Reactor Vessel and Large Component Inspection Using X-Ray Backscatter Radiography by Selective Detection", Proc 2006 International Congress on Advances in Nuclear Power Plants ICAPP, Reno, Jun. 2006, 9 pgs.

Su, "Fundamental Analysis and Algorithms for Development of a Mobile Fast-Scan Lateral Migration Radiography System," Ph.D. Dissertation, University of Florida, May 2001, 132 pgs.

Su et al., "X-ray Lateral Migration Radiography System for the Application of Land Mine Detection," Proceedings of SPIE 45th Annual Meeting, Symposium on Optical Science and Technology, vol. 4142, pp. 150-160, San Diego, Jul. 2000.

Watanabe et al., "Computational Methods for Shape Restoration of Buried Objects in Compton Backscatter Imaging," Nuclear Science and Engineering, vol. 122, pp. 55-67, Jan. 1996.

Wehlburg et al., "Experimental Measurement of Noise Removal Techniques for Compton Backscatter Imaging as Applied to the Detection of Landmines," SPIE Proceedings on Detection and Remediation Technologies for Mine and MinelikeTargets, vol. 2765-51, pp. 502-511, Apr. 1996.

Wehlburg et al., "Geometric Considerations Relating to Lateral Migration Radiography (LMBR) as Applied to the Detection of Landmines," SPIE Proceedings on Detection and Remediation Technologies for Mine and Minelike Targets II,vol. 3079, pp. 384-393, Apr. 1997.

Wehlburg et al, "Image Restoration Techniques Using Compton Backscatter Imaging for Detection of Buried Landmines," SPIE Proc on Detection Technologies for Mine and Minelike Targets, vol. 2496, Apr. 1995, pp. 336-347.

Wells et al., "Lateral Migration Measured Image Signatures in the Detection and Identification of Buried Land Mines", SPIE Proc on Detection and Remediation Technologies for Mines and Minelike Targets IV, vol. 3710, pp. 906-916, Apr. 1999.

American Science and Engineering, "Products and Solutions, Securing Ports, Border Crossings and High Threat Facilities and Events", retrieved Jun. 8, 2009 at http://www.as-e.com/products_solutions/index.asp, 2 pgs.

Nucsafe, "Backscatter Radiography, SXI Scatter X-Ray Imaging", retrieved on Jun. 8, 2009 at http://www.nucsafe.com/cms/Backscatter+Radiography/79.html, 2 pgs.

Rapiscan Systems, retrieved Jun. 8, 2009 at http://rapiscansystems.com, 1 pgs.

Shedlock, "XRay Backscatter Imaging for Radiography by Selective Detection and Snapshot: Evolution, Development, and Optimization", Ph.D. Thesis, The University of Florida, Gainesville, 2007, 98 pgs.

University of Florida, "Scatter X-Ray Imaging (SXI)", retrieved on Jun. 8, 2009 at http://sxi.nre.ufl.edu, 1 pg.

Wikipedia, "Backscatter X-Ray", retrieved on Jun. 8, 2009 at http://en.wikipedia.org/wiki/Backscatter_X-ray, 2 pgs.

European Search Report mailed Mar. 11, 2011 for Application No. PCT/US2010/035909.

* cited by examiner

RAPID ASSEMBLY AND OPERATION OF AN X-RAY IMAGING SYSTEM

TECHNICAL FIELD

The present disclosure pertains to X-ray imaging, and more specifically, rapid assembly and operation of an X-ray imaging system.

BACKGROUND

Maintenance is an ongoing occurrence for vehicles and structures that typically have a relatively long operational lifespan. Examples of vehicles that typically undergo maintenance include aircraft, maritime vessels, automobiles, and other large investment assemblies. Examples of structures that typically undergo maintenance include petrochemical facilities, power generation facilities, nuclear facilities, water treatment plants, etc. . . . Routine maintenance for such vehicles and structures may advantageously extend the operational lifespan of the objects.

Inspection of the an object's structure during maintenance is often important to capture normal wear and tear, such as corrosion and cracking, as well as the presence of foreign object debris (FOD). Since the interior structure of some objects such as aircrafts is often difficult to access, one technique frequently used to inspect the object includes disassembling it. Although disassembly provides access to interior surfaces that are otherwise difficult to access, this technique is often time consuming and expensive.

An alternative technique for performing maintenance utilizes X-ray imaging. X-ray imaging involves generating images of the object using an X-ray imaging system. One advantage of X-ray imaging is that it reduces maintenance cycle time since it may not require disassembly in order to inspect interior surfaces.

Maintaining objects using X-ray imaging is often labor intensive, limited to generating images which fall within the field of view of the X-rays, and potentially generates unwanted radiation. For example, in situations where the X-ray field of view is smaller than the object under inspection, the X-ray system may require continuous reorientation during the imaging operations. Re-orienting the field of view of the X-rays may be challenging since it can require labor intensive tooling operations. Often times, re-positioning of the system requires removing a high voltage power cable from the X-ray tube prior to performing the tooling operation. Since many X-ray high voltage power cables require greasing every time they are connected to or disconnected from the X-ray tube, time consuming labor is involved every time the high voltage cable is removed from the X-ray tube.

Furthermore, disassembly and reassembly of the systems are often labor intensive and require various tools. Disassembly and assembly may be required to transport the system such as when the system maintains more than one object, when the service location varies, or when the system is stored. Often, disassembly and reassembly requires labor intensive tooling operations including disconnecting the imaging system from the high voltage power supply. In addition, it often takes multiple personnel to move the system physically.

SUMMARY

Methods and systems for rapid assembly and operation of an X-ray imaging system are disclosed. In one embodiment, an X-ray imaging system generates an X-ray image of an object. The X-ray imaging system may include an X-ray tube to generate X-rays and a rotational collimator to direct the X-rays at the object. The rotational collimator is rotatable through an angular field of view to project an X-ray field of view on the object. A detector array may receive scattered X-rays to generate the image of the object. The system may also include an X-ray tube alignment mechanism to align the X-ray tube with respect to the X-ray imaging system. Rotation and linear mechanisms may enable rotation of the X-ray tube to inspect various portions of the object as well as linear movement of the X-ray imaging system to inspect further portions of the object.

In another embodiment, a method of generating an X-ray image of an object includes positioning an X-ray imaging system on a rail unit. An X-ray tube of the X-ray imaging system generates X-rays and directs the X-rays at the object within an X-ray field of view. In order to capture various portions of the object, the X-ray tube may rotate and move linearly without using tools. The X-ray tube may rotate about a roll axis to move the X-ray field of view up and down on the object. Additionally, the X-ray tube may rotate about a yaw axis to move the X-ray field of view back and forth on the object. Furthermore, the X-ray imaging system may move linearly on the rail unit to further move the X-ray field of view back and forth on the object.

In a further embodiment, a system for performing maintenance on an object includes an X-ray imaging unit. The X-ray imaging unit includes an X-ray tube to generate the X-rays and a detector array to receive scattered X-rays. One or more rotation mechanisms direct the generated X-ray beam to various portions of the object. The X-ray imaging unit may also include a track unit to move the X-ray imaging system linearly.

The features, functions, and advantages may be independently achievable in various embodiments of the present disclosure or combinable in yet other embodiments.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Overview

As discussed above, although X-ray imaging may advantageously reduce vehicle maintenance cycle time, further improvements are desirable. Techniques for further improving vehicle maintenance cycle time and reducing lost profits resulting from vehicle downtime time are disclosed herein. Some techniques include reducing assembly and operational tooling requirements of an X-ray imaging system. Other techniques involve improving the mobility of the X-ray imaging system. An X-ray imaging system having parts which are easy to assemble improves maintenance cycle time by reducing the tooling and labor requirements. In addition, linear and rotational mechanisms allow for efficient rotation of an X-ray field of view both during an initial set-up of the X-ray imaging system as well as during operation of the X-ray imaging system. As discussed herein, the techniques may be implemented on structures, which includes without limitation, aircraft, maritime vessels, spacecraft, motor vehicles, mechanical devices, petrochemical facilities, power generation facilities, nuclear facilities, water treatment plants, and other structures of or machines that receive maintenance.

Illustrative System

Figure 1:
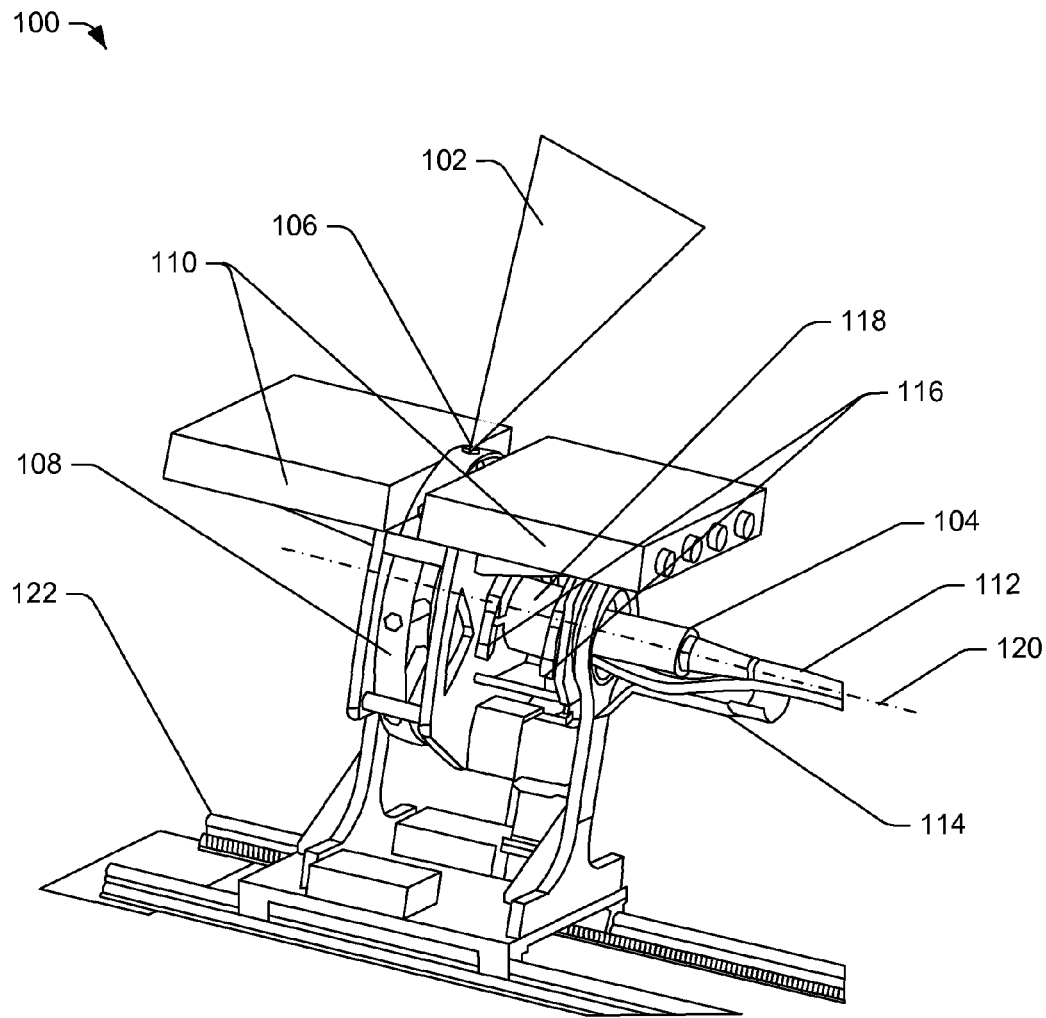
FIG. 1 is an isometric schematic diagram of an illustrative X-ray imaging system.

FIG. 1 is a schematic diagram of an illustrative X-ray imaging system 100. In one embodiment, the X-ray imaging system 100 is an X-ray backscatter system. An X-ray backscatter system may be advantageous over transmission X-ray systems since an X-ray backscatter system can be used to inspect structures from one side since the means of X-ray generation and detection can be placed on the same side. Another advantage is that X-ray backscatter typically projects less radiation than a transmission X-ray system and so requires a smaller exclusion area for radiation safety. As illustrated in FIG. 1, the X-ray imaging system 100 inspects an object (not shown) by projecting an X-ray field of view 102 onto the object under inspection. An X-ray tube 104 generates X-rays. The X-rays then passes through one or more apertures 106 of a rotational collimator 108 to generate the X-ray field of view 102. A detector array 110 of the X-ray imaging system 100 receives at least a portion of the X-rays as it is scattered from the object to generate an image of an object under inspection.

The X-ray tube 104 may use any technique well known in the art to generate the X-rays. In one or more embodiments, the X-ray tube 104 is a vacuum tube and includes a cathode to emit electrons into the vacuum. An anode collects the electrons emitted from the cathode to establish an electrical current through the X-ray tube 104. To generate the X-rays, electrons are boiled off the cathode and collide with the anode under a high energy electric field. If the colliding electrons have sufficient energy, they can knock an electron out of an inner shell of the target metal atoms. X-ray photons with precise energies are emitted when electrons from higher states drop down to fill the vacancy created when the electron is knocked out of the inner shell.

A high voltage power cable 112 may connect the X-ray imaging system 100 to a power source (not shown). In one embodiment, the high voltage power cable 112 is a high voltage cable that supplies power to the X-ray tube 104. The power source may be immobile or preferably, the power source may be positioned on a mobile container (discussed further below and illustrated in FIG. 3). If the power source is positioned on a mobile container, then the X-ray imaging system 100 may advantageously move a distance further than the length of the high voltage power cable 112 by moving the container along with the X-ray imaging system 100. For example, if the X-ray imaging system 100 inspects an object that is longer than the length of the high voltage power cable 112, then the X-ray imaging system 100 is able to continually inspect the object by moving the container along with the X-ray imaging system without having to power off the X-ray tube 104, without having to disconnect the high voltage power cable 112 from the X-ray tube 104, and further without having to dissemble and reassemble the X-ray imaging system 100.

Since many high voltage power cables 112 generally require greasing every time they are connected to or disconnected from the X-ray tube 104, it is desirable to assemble the X-ray imaging system 100 without having to disconnect the X-ray tube 104 from the high voltage power cable 112. In one embodiment, the high voltage power cable 112 is connected to the X-ray tube 104 of the X-ray imaging system 100 such that the X-ray tube 104 along with the high voltage power cable 112 may be inserted together into the X-ray imaging system 100 without using tools and without disconnecting the X-ray tube 104 from the power supply. Likewise, in such embodiment, the high voltage power cable 112 together with the X-ray tube 104 may be removed from the X-ray imaging system 100 without using tools and without disconnecting the X-ray tube 104 from the power supply. In one embodiment, the X-ray imaging system 100 may include a power cord support element 114 to support the high voltage power cable 112 and provide strain relief to the system.

As described further below with reference to FIG. 2, the X-ray tube 104 may be inserted into and removed from the X-ray imaging system 100 using an X-ray tube alignment mechanism 200. In an illustrative embodiment, the X-ray tube alignment mechanism 200 aligns the X-ray tube 104 as it is inserted into the X-ray imaging system 100 without using tools. The X-ray tube 104 may be secured to the X-ray imaging system 100 using any conceivable X-ray tube 104 attachment mechanism. With continuing reference to FIG. 1, one or more clamp mechanisms 116 secure the X-ray tube 104 to the X-ray imaging system 100 without using tools. It is advantageous to secure the X-ray tube 104 to the X-ray imaging system 100 without using tools since it enables rapid assembly of the X-ray imaging system 100. In addition to supporting the X-ray tube 104, the clamp mechanisms 116 may also act as a radiation shield around the tube. This not only protects against unwanted radiation, but it also reduces noise in the image by keeping radiation from flowing into a backside of the detector array 110. The X-ray tube 104 may have an X-ray tube shield 118 to further protect against unwanted radiation. The X-ray tube shield 118 may be cylindrical so that it easily fits around the X-ray tube 104.

As further illustrated in FIG. 1, the X-rays pass from the X-ray tube 104 through the rotational collimator 108 to the object. The rotational collimator 108 may share a common centerline axis 120 with the X-ray tube 104 so that the X-ray tube 104 may be inserted directly into the rotational collimator 108. In one embodiment, the rotational collimator 108 has one or more apertures 106 such that as the rotational collimator 108 rotates about the common centerline axis 120, at least a portion of the X-rays passes through one or more apertures 106. Although FIG. 1 shows the rotational collimator 108 having eight apertures 106, any number of apertures 106 may be provided.

In the illustrated implementation, the X-ray tube 104 inserts directly into the rotational collimator 108 and the rotational collimator 108 rotates about the common centerline axis 120 while the X-ray tube 104 remains stationary. Although any mechanism may enable a rotation of the rotational collimator 108 while the X-ray tube 104 remains stationary, a first pass collimator (not shown) may be used to shape the X-rays. The first pass collimator may be attached to and surround the X-ray tube 104. The first pass collimator includes one or more apertures to shape the X-rays. The rotational collimator 108 interfaces with the first pass collimator such that the rotational collimator 108 is able to rotate about the X-ray tube 104 even if the X-ray tube remains stationary while preventing unintended leakage between the two collimators. The first pass collimator is desirable because it allows the X-ray tube 104 to slip-fit into the X-ray imaging system 100 while still allowing the rotational collimator 108 to rotate while preventing leakage from the X-ray tube 104.

In an alternative embodiment, the rotational collimator 108 may rotate about the centerline axis along with the X-ray tube 104 such that the X-rays passes through a single aperture of the rotational collimator 108 as the rotational collimator 108 rotates with the X-ray tube 104. In a further alternative embodiment, the rotational collimator 108 along with the anode of the X-ray tube 104 may rotate together with respect to the X-ray tube 104 to inspect the object.

As noted above, a detector array 110 may receive the X-rays as it is scattered from the object to generate an image of the object. Although two detectors are illustrated in FIG. 1, the detector array 110 may include one or more detectors. For example, the detector array 110 may consist of four detectors rather than two detectors. Additionally, the number and arrangement of detectors in the array is versatile such that the same X-ray imaging system can image a first object or a first part of a first object using a first count of detectors arranged in a first order and then the same X-ray imaging system can image a second object or a second part of the first object using a second count of detectors arranged in a second order. In one embodiment, the detectors of the detector array 110 are interchangeable such that the detectors can be positioned in any order.

The X-ray imaging system 100 may be positioned upon a track unit 122 for added mobility. As described further below, a track unit mechanism of the track unit 122 allows the entire X-ray imaging system 100 to move linearly. In one embodiment, the track unit mechanism moves the X-ray imaging system 100 along the track unit 122 automatically or manually while the X-ray imaging system 100 operationally inspects the object. In an alternative embodiment, the track unit mechanism moves the X-ray imaging system 100 along the track unit 122 during an initial set-up of the X-ray imaging system to orient the X-ray imaging system as desired. The track unit mechanism advantageously enables the X-ray imaging system 100 to continuously inspect various areas of an object significantly larger than the projected X-ray field of view on the object by moving the X-ray imaging system 100 along the track unit.

Illustrative X-Ray Tube Alignment Mechanism

Figure 2:
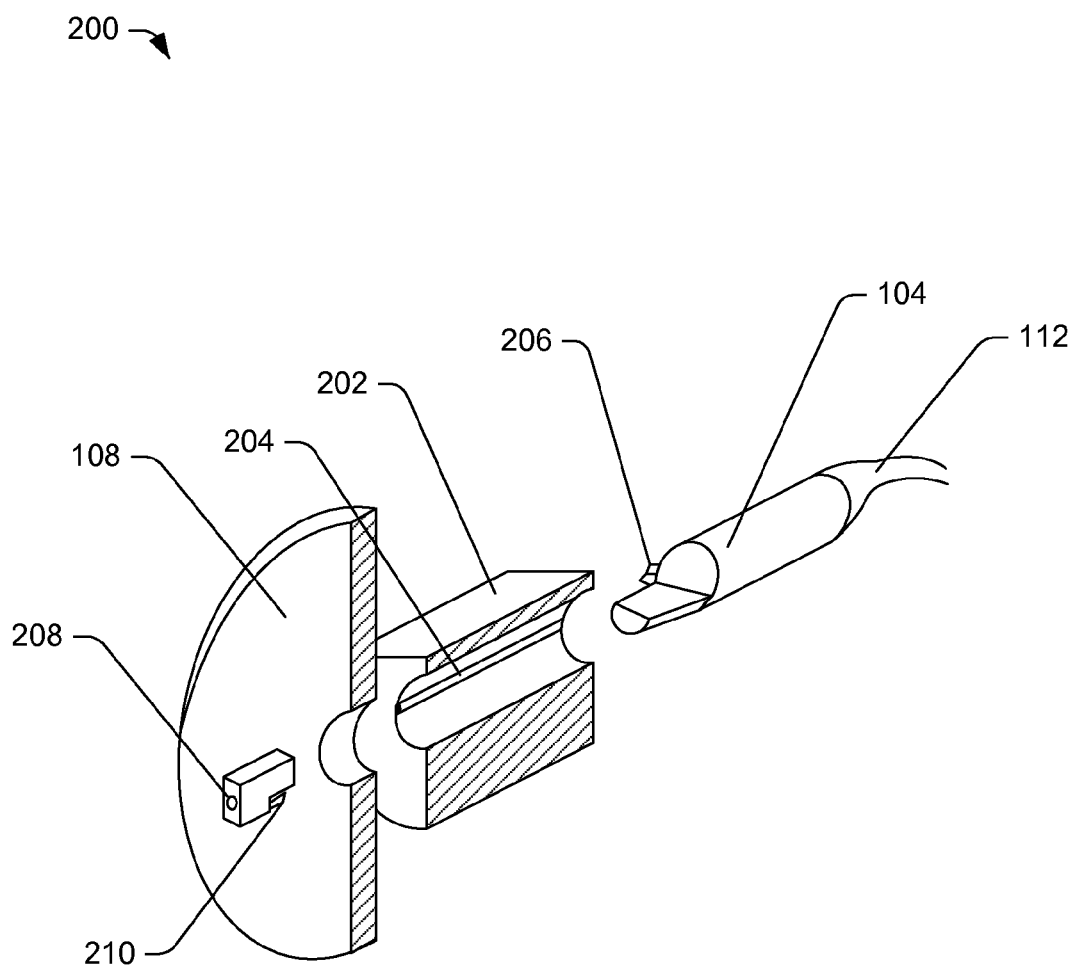
FIG. 2 is an isometric schematic diagram of an illustrative X-ray tube alignment mechanism.

FIG. 2 is an isometric schematic diagram of an illustrative X-ray tube alignment mechanism 200. As noted above, the X-ray tube alignment mechanism 200 orients the X-ray tube 104 as it slides into the X-ray imaging system 100 without the use of tools.

As illustrated in FIG. 2, an X-ray tube housing element 202 of the X-ray imaging system 100 may include a guide mechanism to assure that the X-ray tube 104 is properly oriented with respect to the rotational collimator 108. For example, the X-ray tube 104 may include a guide slot 204 such that a guide pin 206 located on the end of the X-ray tube 104 slides into the guide slot 204 as the X-ray tube 104 is inserted into or removed from the X-ray tube housing element 202. The guide slot 204 of the X-ray tube housing element 202 ensures a proper rotational orientation of the X-ray tube 104 as it is inserted into the X-ray tube housing element 202. For example, the X-ray tube 104 may only be inserted into the X-ray tube housing element 202 if the guide pin 206 is properly aligned with the guide slot 204. In one embodiment, the X-ray tube housing element 202 may be part of the rotational collimator 108. In an alternative embodiment, however, the X-ray tube housing element 202 may be separate from the rotational collimator 108.

The X-ray tube alignment mechanism 200 may include a safety interlock 208 to determine whether the X-ray tube 104 is properly aligned within the X-ray tube housing element 202. The safety interlock 208 may then communicate an alignment indication (whether or not the X-ray tube 104 is properly aligned within the X-ray tube housing element 202). If the safety interlock 208 communicates an alignment failure communication (communication indicating that the X-ray tube 104 is not properly aligned within the X-ray tube housing element 202), then the X-ray tube 104 may be prevented from generating the X-rays. In a further embodiment, the X-ray tube 104 may be prevented from generating the X-rays until the safety interlock 208 communicates an alignment pass communication (communication indicating that the X-ray tube 104 is properly aligned within the X-ray tube housing element 202). If the X-ray tube 104 becomes unaligned while the X-ray tube 104 is operatively emitting X-rays, an alignment failure communication may automatically shut off the X-ray tube 104. If the X-ray tube 104 becomes properly aligned within the X-ray tube housing element 202, an alignment pass communication may automatically commence a generation of X-ray beams from the X-ray tube 104.

The safety interlock 208 may be any mechanism that identifies an alignment of the X-ray tube 104 with the X-ray tube housing element 202. For example, the safety interlock 208 may be a mechanical plunger switch, an optical interlock, a proximity sensor, and so forth. In one non-limiting embodiment, as illustrated in FIG. 2, the safety interlock 208 is a mechanical plunger switch wired to an X-ray safety system such that the plunger switch communicates the alignment indication to an electrical system (not shown) of the X-ray imaging system 100. In such an embodiment, the electrical system may prevent the X-ray tube 104 from generating the X-rays if the mechanical switch communicates an alignment failure communication to the electrical system. Further, the electrical system may prevent the X-ray tube 104 from becoming operational until the safety interlock 208 communicates an alignment pass communication to the electrical system. Although the safety interlock 208 illustrated in FIG. 2 is a mechanical plunger switch, any other safety interlock 208 mechanism may be provided.

As further illustrated in FIG. 2, an X-ray tube housing element 202 of the X-ray imaging system 100 may include a stopper mechanism 210 to assure that the X-ray tube 104 is inserted a desired distance into the X-ray imaging system 100. In one embodiment, the X-ray tube housing element 202 includes a stopper mechanism 210 set at the desired distance such that the X-ray tube 104 may only be slide into the X-ray tube housing element 202 until the X-ray tube 104 contacts the stopper mechanism 210. Although the stopper mechanism 210 may be any type of mechanism, in one non limiting embodiment, the stopper mechanism 210 is a set screw.

Illustrative Track Unit

As noted above, the X-ray imaging system may be positioned on a track unit 122. In an illustrative embodiment, a track unit mechanism moves the X-ray imaging system linearly along the track unit 122 such that the X-ray imaging system may continuously inspect an object without disassembling the X-ray imaging system and without powering off the X-ray tube 104. Although the track unit 122 illustrated in FIG. 1 shows the track unit 122 having two rails, any number of rails may be provided. For example, the track unit 122 may only have a single rail. The X-ray imaging system 100 movably attaches to the rails of the track unit 122.

The track unit 122 may include multiple connectable track segments to provide for rapid assembly, disassembly, and storage. In addition, multiple track segments enable a limited number of track segments to be rearranged to create an infinitely long track unit 122. For example, the track segments may be identical to one another such that any segment may connect to any other segment. Although FIG. 1 illustrates the track segments aligned in a straight line, the track segments may also include curved segments. A track unit 122 comprised of one or more curved track segments may advantageously allow the X-ray imaging system 100 to move in various directions including a circle.

Since the track segments are connectable to any other segments, a limited number of track segments may create an infinitely long track unit and hence may move the X-ray imaging system 100 a distance greater than the combined length of the individual track segments. For example, if the track unit 122 includes a four track segments then as the X-ray imaging system moves from the first track segment to the second track segment, the first track segment may be moved from the back end of the track unit 122 to the front end of the track unit 122 to elongate the track unit. The first track segment may be moved from the back end of the track unit 122 to the front end of the track unit 122 by un-connecting it from the back end of the track unit and then re-connecting it to the front end. Similarly, every time the X-ray imaging system 100 moves off of a track segment, that track segment may be move to the front of the track unit 122 so that the X-ray imaging system 100 can move along the track unit 122 at a constant rate of speed without running out of track.

In one embodiment, the track segments may move from one end of the track unit 122 to the other end of the track unit 122 manually. In such embodiment, the X-ray tube 104 includes a shield mechanism such that a person may walk up to the X-ray imaging system 100 and move the track segments from the end of the track unit 122 to the front of the track unit 122 manually without exposure to unwanted radiation.

The track unit 122 may also include an end of track detection unit to detect when the X-ray imaging system approaches the end of the track unit. The end of track detection unit may be placed on the X-ray imaging system, or alternatively the end of track detection unit may be placed on the track unit. Additionally, in a further embodiment, the end of track detection unit may be placed both on the X-ray imaging system 100 as well as on the track unit 122. The end of track detection unit may be any mechanism that identifies proximity of the X-ray imaging system 100 with respect to the end of the track unit 122. For example, the end of track detection unit may be a mechanical sensor or an optical sensor.

The end of track detection unit may also be linked to the track unit mechanism such that the end of track detection unit responds when the end of track detection unit senses the X-ray imaging system 100 approaching the end of the track unit 122. The end of track detection unit may respond by using one or more methods to prevent the X-ray imaging system 100 from running off the end of the track unit 122. In one embodiment, the end of track detection unit responds by generating an alarm such as an audio or visual alarm. In another embodiment, the end of track detection unit may respond by causing the X-ray imaging system 100 to slow down or stop moving along the track unit 122 altogether. Alternatively, the end of track detection unit may respond by both generating an alarm as well as causing the X-ray imaging system 100 to slow down or stop moving along the track unit 122.

Although FIG. 1 illustrates the track unit 122 on the ground, any orientation may be provided. For example, the track unit 122 may be bolted to the wall such that the X-ray imaging system 100 moves along the wall.

As discussed above, the X-ray imaging system 100 includes a high voltage power cable 112 which connects a power source to the X-ray tube 104. As further discussed above, the power source may preferably be positioned on a mobile container. Positioning the power source on a mobile container advantageously allows the X-ray imaging system 100 to move along the track unit 122 while continuously inspecting the object without having to power down the X-ray tube 104 and without having to disconnect the high voltage power cable 112 from the X-ray tube 104. In other words, positioning the power source on a mobile container allows the power source to move along with the X-ray imaging system 100 as the X-ray imaging system 100 inspects the object.

Illustrative Mobile Container

Figure 3:
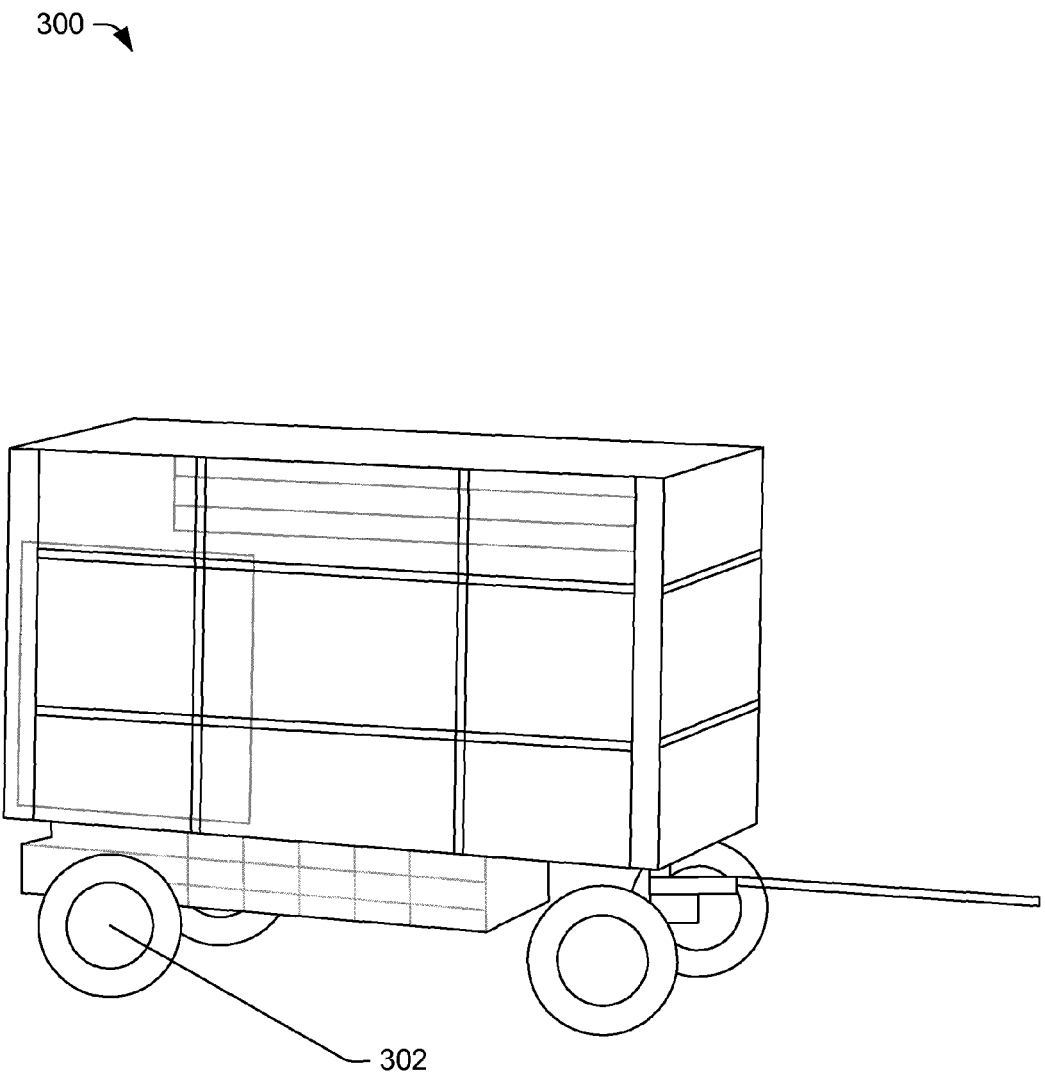
FIG. 3 is an isometric schematic diagram of an illustrative X-ray imaging system mobile container.

FIG. 3 is an isometric depiction of a mobile container 300 for an illustrative X-ray imaging system. As discussed above, the mobile container 300 is utilized during operation of the X-ray imaging system 100, during storage of the X-ray imaging system 100, as well as for shipment of the X-ray imaging system 100.

The mobile container 300 may store one or more elements of the X-ray imaging system 100. In one embodiment, when the X-ray imaging system 100 is not operational, the mobile container 300 stores all elements of the X-ray imaging system 100 including the power supply, the high voltage power cable 112, and the detector array 110. In a further embodiment, the mobile container 300 may additionally store the track unit 122. The mobile container 300 may have a plurality of wheels 302 to move the mobile container 300. In addition, the wheels of the mobile container may also include a locking mechanism. When engaged, the locking mechanism may prevent the wheels from rotating.

In an operational embodiment, the mobile container 300 may roll the X-ray imaging system 100 to a desired inspection location for rapid assembly of the X-ray imaging system. One or more walls of the mobile container 300 may be removed or folded down to allow easy access to the elements stored in the mobile container 300. Once the X-ray imaging system 100 is assembled and operational, the mobile container 300 remains tethered to the X-ray imaging system (not shown) to hold one or more elements of the X-ray imaging system 100 while the X-ray imaging system inspects the object. In an illustrative embodiment, the mobile container 300 holds at least the power supply to the X-ray imaging system 100 during operation. However, the mobile container 300 may hold more elements if desired. For example, the mobile container 300 may also hold a chiller unit.

It is advantageous for the mobile container 300 to hold at least the power supply while remaining tethered to the X-ray imaging system 100 during operation for at least two reasons. First, it allows the mobile container 300 to roll during operation of the X-ray imaging system 100. For example, the track unit mechanism may move the X-ray imaging system 100 while pulling along the mobile container 300 to inspect the object continuously. Second, if the mobile container 300 is tethered to the X-ray imaging system 100 then the high voltage power cable 112 does not have to be disconnected from the X-ray tube 104 in order to store the X-ray imaging system 100 in the mobile container 300.

The walls and roof the mobile container 300 may fold flat so that they can lie out of the way when they are not in use. All sides of the mobile container 300 including the roof may be individually removable such that the mobile container 300 can be used in any environmental condition. For example, if the mobile container 300 is used in the rain then the roof and ends of the cart may be left on the mobile container 300 during operation to protect the contents of the mobile container 300 from the rain.

The mobile container may also include its own power cable to connect the mobile container to a power source. For example, the mobile container may include its own power cable to connect the mobile container to a building power supply, a diesel generator, or a gas generator. Alternatively, the mobile container may include a generator such that the mobile container is its own power source.

The mobile container 300 may also act as a shipment container to ship all elements of the x-ray imaging system 100 from one place to another.

Illustrative Implementation

Figure 4:
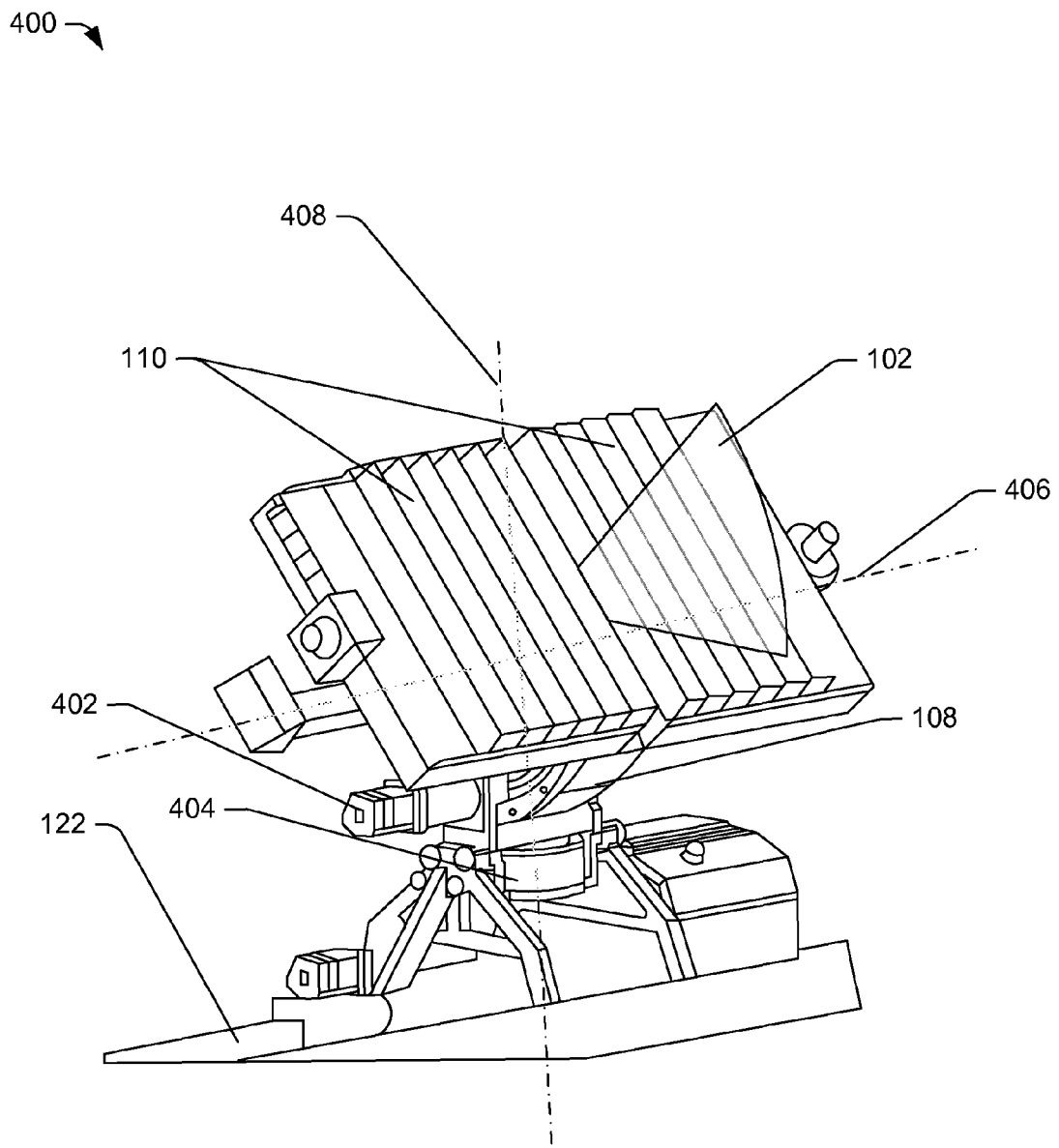
FIG. 4 is an isometric schematic illustration of an operational embodiment of the X-ray imaging system.

FIG. 4 schematically illustrates an operational embodiment of the X-ray imaging system 400. As described above, the X-ray imaging system may be assembled using minimal tools and without having to connect or disconnect the high voltage power cable (not shown) from the X-ray tube (not shown). The various elements of the X-ray imaging system may be assembled in any desirable order. In a non-limiting illustrative embodiment, the track unit 122 is set up, the X-ray imaging system is placed on the track unit, the detector array 110 is clamped to the X-ray imaging system, the X-ray tube along with the high voltage power cable are inserted into the X-ray imaging system, and the X-ray tube is clamped to the X-ray imaging system all without the use of tools or removable fasteners. The X-ray imaging system may be assembled inside of an object under inspection such that the object is inspected from the inside or the X-ray imaging system may be assembled outside of the object to inspect the object from the outside.

After assembly, X-ray imaging system 400 may be prepositioned. Prepositioning the X-ray imaging system may include moving the X-ray imaging system linearly along the track unit 122 to a desired position. A roll mechanism 402 may further preposition the X-ray imaging system by rotating one or more elements of the X-ray imaging system as described further below. A yaw mechanism 404 may further preposition the X-ray imaging system by rotating one or elements of the X-ray imaging system as described further below.

After prepositioning, the X-ray imaging system may inspect an object by emitting X-rays through one or more of the apertures in the rotational collimator 108 to direct an X-ray field of view 102 at the object. As discussed above, the X-ray field of view 102 is the projection of the X-rays on the object under inspection. In one embodiment, the rotational collimator 108 directs the X-ray field of view 102 at the object by rotating about the X-ray tube. Alternatively, a roll mechanism 402 may rotate one or more elements of the X-ray imaging system as described further below to direct the X-ray field of view 102. The X-ray imaging system may continue to inspect the object further by translating the directed X-ray field of view 102 with respect to the object.

In one embodiment described further below, the roll mechanism 402 moves the directed X-ray field of view about the object to inspect the object further by rotating one or more elements of the X-ray imaging system. In another embodiment as described further below, the yaw mechanism 404 moves the directed X-ray field of view to inspect the object further by rotating one or more elements of the X-ray imaging system. In another embodiment, the X-ray imaging system moves linearly along the track unit 122 to move the directed X-ray field of view to further inspect the object. Additionally, any combination of the roll mechanism 402, yaw mechanism 404, and linear movement along the track unit 122 may be used together or separately to further inspect the object.

As mentioned directly above, the roll mechanism 402 may rotate one or more elements of the X-ray imaging system to preposition the X-ray imaging system, to direct the X-ray field of view 102, and/or to move the directed X-ray field of view about the object under inspection. The roll mechanism 402 may rotate one or more X-ray imaging system roll elements about a roll axis 406 to preposition the X-ray imaging system, to direct the X-ray field of view 102, and/or to move the directed X-ray field of view. The roll axis 406 may be any desirable axis parallel to the X-ray tube centerline. In one embodiment, the roll axis 406 is the same as the common centerline axis 120 of FIG. 1; however, in an alternative embodiment, the roll axis 406 may be different from the common centerline axis 120.

In one embodiment, the roll mechanism 402 rotates at least the X-ray tube and the detector array 110 about the roll axis 406. In such an embodiment, the roll mechanism 402 may further rotate the X-ray tube and the detector array 110 while the rotational collimator 108 remains independently rotational about the same roll axis 406. Additionally, the roll mechanism 402 may rotate the X-ray tube, the detector array 110, and the high voltage power cord support element (114 of FIG. 1) along with the X-ray tube and the detector array 110. It may be advantageous to roll the high voltage power cord support element along with the X-ray tube and the detector array 110 to prevent the high voltage power cable from becoming twisted between the high voltage power cord support element and the roll axis 406 as the roll mechanism 402 rolls the roll elements.

The roll mechanism 402 may rotate the one or more roll elements about the roll axis 406 to any angle within a 360 degree range. In one embodiment, a mechanical device such as a pull pin constrains the roll of the roll elements about the roll axis 406. In such an embodiment, the roll elements rotate in pre-defined angular increments from one pin hole to the next pin hole. For example, the pin holes may be placed at fifteen degree increments so that the roll mechanism 402 may rotate the roll elements to a fifteen degree angle, a thirty degree angle, a forty-five degree angle, a sixty degree angle, etc. When the roll elements are rolled to the desired angular orientation, the pull pin is placed into the corresponding pin hole to stabilize the roll mechanism 402. In an alternative embodiment, a motor may roll the roll elements about the roll axis 406. In such an embodiment, an angular orientation of the roll elements is not limited to the size of the pin or to the location of pin holes. Rather, a motor enables the roll mechanism 402 to roll the roll elements to any desired angular orientation within a 360 degree range.

If a motor is used to roll the roll elements, the roll mechanism 402 may roll the elements while the X-ray imaging system is operatively imaging an object to continuously generate an image of the object. In such an embodiment, the high voltage power cable does not have to be disconnected from the X-ray imaging system in order to roll the roll elements about the roll axis 406. Alternatively, the X-ray imaging system may be powered off when rotating the roll elements such as to preposition the X-ray imaging system.

As mentioned above, the yaw mechanism 404 may rotate one or more elements of the X-ray imaging system to move the directed X-ray field of view 102 about the object under inspection. In addition to moving the directed X-ray field of view 102, the yaw mechanism 404 may also rotate one or more elements of the X-ray imaging system to preposition the X-ray imaging system. The yaw mechanism 404 may rotate one or more of the X-ray imaging system yaw elements about the yaw axis 408 to move the directed X-ray field of view 102. Although the yaw axis 408 may be placed at any location on the X-ray imaging system, the yaw axis 408 is preferably positioned perpendicular to a base of the track unit 122. In one embodiment, the yaw axis 408 may be positioned on a vector defined by the intersection of a plane defined by the rotational collimator 108 and a vertical plane including the roll axis 406.

The yaw mechanism 404 may rotate the one or more yaw elements of the X-ray imaging system about the yaw axis 408 to any angle within a 360 degree range. The one or more yaw elements may be the same elements as the one or more roll elements; however, the yaw elements are not limited to being the same elements as the roll elements. In one embodiment, the yaw mechanism 404 rotates at least the X-ray tube and the detector array 110 about the yaw axis 408. For example, the yaw mechanism 404 may rotate the X-ray tube and the detector array 110 about the yaw axis 408 while the rotational collimator 108 remains independently rotational about the common centerline axis.

In one embodiment, a mechanical device may yaw the yaw elements about the yaw axis 408 to any desired angular orientation within a 360 degree range. The mechanical device may yaw the yaw elements while the X-ray imaging system is operatively imaging an object such that a continuous image of the object may be generated. In such an embodiment, the high voltage power cable does not have to be disconnected from the X-ray imaging system in order to yaw the yaw elements about the yaw axis 408. For example, a motor may yaw the yaw elements while the X-ray imaging system is operatively imaging an object without disconnecting the high voltage power cable from the X-ray imaging system.

The combination of the roll mechanism 402 with the yaw mechanism 404 advantageously allows the X-ray imaging system to produce a spherical image by continuously rolling the roll elements and yawing the yaw elements while imaging a spherical structure, for example, without powering off the X-ray tube and without disconnecting the high voltage power cable from the X-ray tube.

Figure 5:
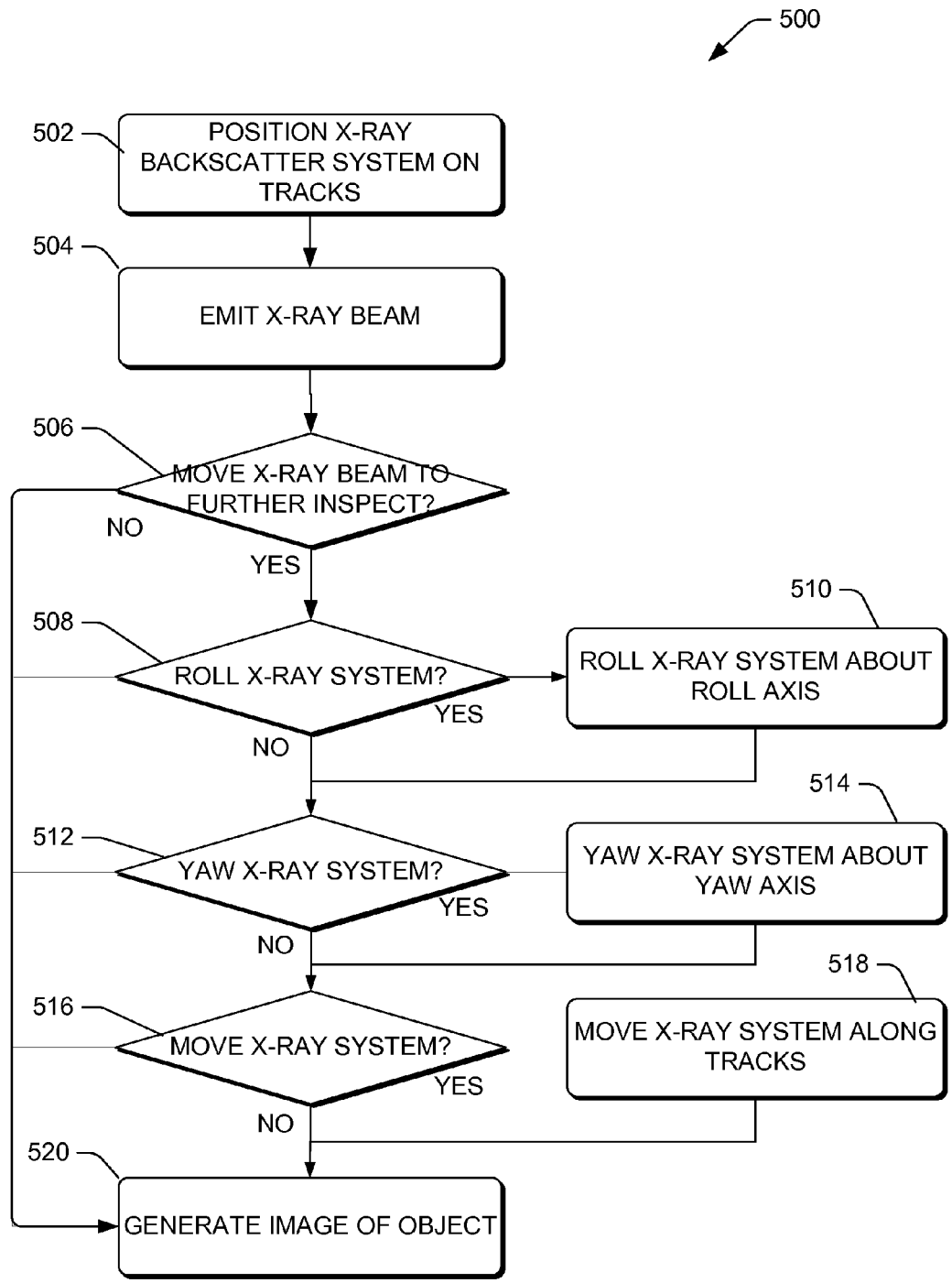
FIG. 5 is a flow diagram of an illustrative operational embodiment of the X-ray imaging system.

FIG. 5 is an illustrative operational embodiment 500 of an X-ray backscatter system. The operational embodiment 500 is illustrated as a collection of blocks in a logical flow graph, which represent a sequence of operations that can be implemented in hardware, software, or a combination thereof. In the context of software, the blocks represent computer-executable instructions that, when executed by one or more processors, cause the one or more processors to perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

The process 500 may be performed, at least in part, by the X-ray imaging system 400 of FIG. 4. At 502, the X-ray backscatter system is positioned on the track unit. Positioning the X-ray imaging system may include placing the X-ray imaging system on the track unit. Positioning the X-ray imaging system may further include prepositioning the X-ray imaging system such as described above. For example, prepositioning the X-ray imaging system may include moving the X-ray imaging system linearly along the track unit 122 to a desired position, rotating one or elements of the X-ray imaging system about the roll axis to a desired location, and/or rotating one or more elements of the X-ray imaging system about the yaw axis to a desired location.

At 504, the X-ray tube operationally emits X-rays at a desired object. A rotational collimator or a roll mechanism may emit the X-rays at the object. For example, the rotational collimator may emit the X-rays at the object by rotating about the X-ray tube. Alternatively, a roll mechanism may rotate one or more elements of the X-ray imaging system to emit the X-rays at the object.

At 506, a determination is made as to whether additional areas of the object are to be inspected. If more areas of the object are to be inspected (i.e., the "Yes" branch from 506), a determination is made at 508 whether the additional elements of the object can be inspected by rolling at least a portion of the X-ray backscatter system. If so (i.e., the "Yes" branch from 508), at least a portion of the X-ray backscatter system is rolled about a roll axis at 510. In the described implementation above, the roll mechanism rotates the X-ray imaging roll elements about the roll axis to capture the additional elements of the object. In one operational mode, the roll mechanism rotates the roll elements while the X-ray backscatter system operatively images the object. In an alternative mode, the X-ray backscatter system is powered off before rotating the roll elements.

Regardless of whether roll is used (i.e., from 510) or is not used to capture other parts of the objects (i.e., the "No" branch from 508), a determination is made whether to yaw the X-ray backscatter system to capture the additional elements of the object that desire inspection. If the yawing X-ray backscatter system enables additional inspection of the object, then at least a portion of the X-ray backscatter system is yawed about a yaw axis at 514. In the described implementation above, the yaw mechanism yaws the X-ray imaging yaw elements about the yaw axis to capture the additional elements of the object. In one operational mode, the yaw mechanism rotates the yaw elements while the X-ray backscatter system operatively images the object. In an alternative embodiment, the X-ray backscatter system is powered off before rotating the yaw elements.

Regardless of whether yaw is used (i.e., from 514) or is not used to capture other parts of the objects (i.e., the "No" branch from 512), a determination is made at 516 whether moving the X-ray backscatter system along the tracks enables additional inspection of the object. If so (i.e., the "Yes" branch from 516), the X-ray backscatter system moves along the tracks. In the described implementation above, the track unit mechanism moves the X-ray backscatter system linearly along the track unit 122.

In one embodiment, the X-ray backscatter system simultaneously rolls at 510, yaws at 514, and moves at 518. In an alternative embodiment, the X-ray backscatter system independently rolls at 510, independently yaws at 514, and independently moves at 518. Alternatively, any combination of rolling, yawing, and moving may achieve the desired image.

At least a portion of the emitted X-ray beam scatters back off the object to generate an image of the object at 520.

Figure 6:
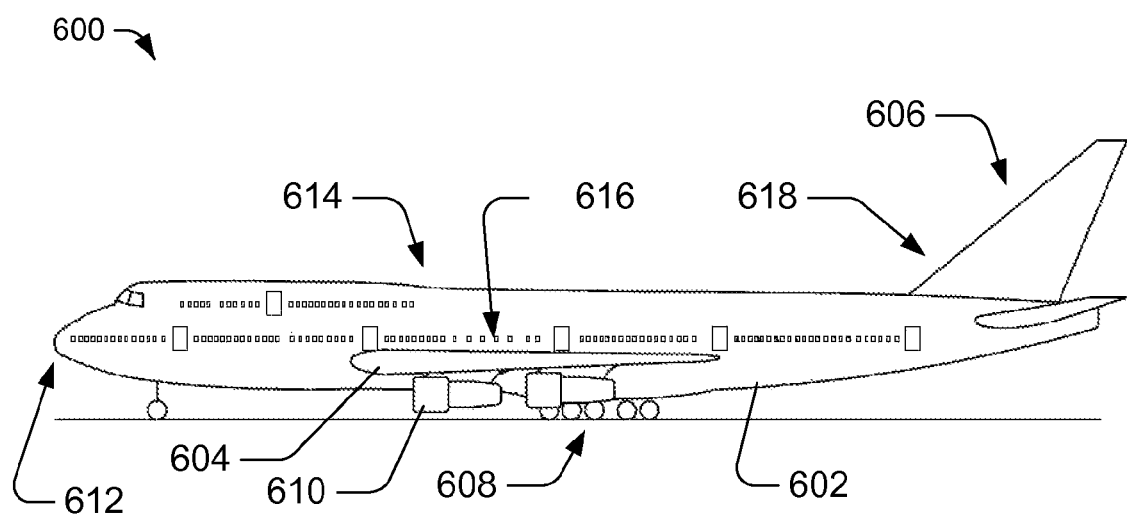
FIG. 6 is a side elevation view of an illustrative aircraft.

FIG. 6 is a side elevational view of an illustrative aircraft 600, which may experience fleet maintenance that is performed using the techniques disclosed herein. One may appreciate that the aircraft 600 may include various known and unknown parts, particularly if the aircraft has been in-service for many years, such as an aircraft assembled for large-scale war service (e.g., circa 1945, etc.) Thus, the X-ray imaging system may generate an X-ray image to identify the presence of corrosion, cracking, and FOD as disclosed herein.

In this embodiment, the aircraft 600 includes a fuselage 602 including wing assemblies 604, a tail assembly 606, and a landing assembly 608. The aircraft 600 further includes one or more propulsion units 610, a control system 612, and a host of other systems and subsystems that enable proper operation of the aircraft 600. One should appreciate that many parts included in an aircraft may be imaged using the X-ray imaging system techniques disclosed herein.

Although the aircraft 600 shown in FIG. 9 is generally representative of a commercial passenger aircraft; the teachings of the present disclosure may be applied to the maintenance, manufacture, and assembly of other structures including passenger aircraft, fighter aircraft, cargo aircraft, rotary aircraft, other types of manned or unmanned aircraft, ground vehicles, ships, petrochemical facilities, power generation facilities, nuclear facilities, water treatment plants, etc. . . .

CONCLUSION

While embodiments of the disclosure have been illustrated and described, as noted above, many changes can be made without departing from the spirit and scope of the disclosure. Accordingly, the scope of the disclosure is not limited by the disclosure of these embodiments. Instead, the disclosure should be determined entirely by reference to the claims that follow.

What is claimed is:

1. An X-ray imaging system, comprising:
an X-ray tube to emit X-rays;
a rotational collimator to direct the X rays being emitted, the rotational collimator sharing a common centerline axis with the X-ray tube;
an X-ray tube alignment mechanism to slideably align the X-ray tube into the X-ray imaging system;
a roll mechanism to enable a roll rotation of at least one element of the X-ray imaging system about the common centerline axis; and
a high voltage power cord support element to support a high voltage power cable operationally linked to the X-ray tube, the high voltage power cord support element rotatable about the common centerline axis via the roll mechanism.

2. The X-ray imaging system of claim 1, wherein the X-ray tube alignment mechanism includes:
a guide slot to align the X-ray tube into the X-ray imaging system;
a clamp mechanism to clamp the aligned X-ray tube to the X-ray imaging system; and
a safety interlock to indicate a proper alignment of the X-ray tube with the X-ray imaging system.

3. The X-ray imaging system of claim 1, wherein the X-ray tube alignment mechanism slideably aligns the X-ray tube into the X-ray imaging system while the X-ray tube is operatively connected to the high voltage power cable.

4. The X-ray imaging system of claim 1, further comprising a detector array to receive one or more scattered X-rays, wherein the roll mechanism enables at least the X-ray tube and the detector array to rotate about the common centerline axis.

5. The X-ray imaging system of claim 1, further comprising a yaw mechanism to enable a yaw rotation of at least the X-ray tube and the detector array about a yaw axis while the X-ray imaging system is operatively emitting X-rays.

6. The X-ray imaging system of claim 1, further comprising a track unit to enable a linear movement of the X-ray imaging system, the track unit including a plurality of interchangeably connectable track segments.

7. The X-ray imaging system of claim 1, further comprising a mobile container to store at least a high voltage power supply, the mobile container being tethered to the X-ray imaging system during operation of the X-ray imaging system.

8. A method of inspecting an object, the method comprising:
positioning an X-ray imaging system on a rail unit, the X-ray imaging system having an X-ray field of view;
securing an X-ray tube to the X-ray imaging system while the X-ray tube is operatively connected to a high voltage power cable, the X-ray tube having the X-ray field of view;
directing the X-ray imaging system to project the X-ray field of view at the object, the directing the X-ray field of view including:
rotating at least one roll X-ray imaging system element about a roll axis to direct the X-ray field of view on a first portion of the object,
rotating at least one yaw X-ray imaging system element about a yaw axis to direct the X-ray field of view on a second portion of the object, and
moving the X-ray imaging system along the rail unit to direct the X-ray field of view on a third portion of the object;
emitting X-rays at the object via the X-ray tube, the X-rays emitted within at least a portion of the X-ray field of view;
receiving scattered X-rays from the object, via a detector array, to generate an image of the object;
storing the X-ray imaging system in a portable container while the X-ray imaging system is operatively connected to a power source; and
supporting a high voltage power cable by a high voltage power cord support element, the high voltage power cord support element being rotatable about the roll axis.

9. The method of claim 8, wherein the rotating at least one roll X-ray imaging system element about the roll axis rotates at least the X-ray tube and the detector array about the roll axis, and further wherein the rotating at least one yaw X-ray imaging system element about a yaw axis rotates at least the X-ray tube and the detector array about the yaw axis.

10. The method of claim 8, wherein:
rotating at least one roll X-ray imaging system element about the roll axis directs the X-ray field of view while emitting the X-rays at the object;
rotating at least one yaw X-ray imaging system element about a yaw axis directs the X-ray field of view while emitting the X-rays at the object; and
moving the X-ray imaging system linearly along the rail unit directs the X-ray field of view while emitting the X-rays at the object.

11. The method of claim 8, wherein the rotating at least one roll X-ray imaging system element about the roll axis includes rotating at least the X-ray tube, the detector array, and the high voltage power cord support element about the roll axis.

12. The method of claim 8, wherein the moving the X-ray imaging system linearly along the rail unit includes:
sensing a proximity of the X-ray imaging system to an end of the rail unit; and
generating a signal when the proximity of the X-ray imaging system to the end of the rail unit is less than a predetermined proximity tolerance level.

13. The method of claim 8, wherein the moving the X-ray imaging system linearly along the rail unit includes moving the mobile container along with the X-ray imaging system while the mobile container is operatively tethered to the X-ray imaging system.

14. The method of claim 8, wherein the emitting X-rays at the object includes rotating a rotational collimator about the roll axis.

15. A vehicle maintenance system, comprising:
an X-ray imaging unit to generate an image of a vehicle, the X-ray imaging unit including:
an X-ray tube to generate X-rays,
a detector array to receive scattered X-rays,
one or more operable rotation mechanisms to rotate at least the detector array about a roll axis and a yaw axis, and
an X-ray tube alignment mechanism to align and clamp the X-ray tube to the X-ray imaging unit;
a track unit mechanism to move the X-ray imaging unit linearly along a track unit while the X-ray imaging unit is operatively connected to a high voltage power source; and
a high voltage power cord support element to support a high voltage power cable, the high voltage power cord support element being rotatable about the roll axis.

16. The vehicle maintenance system of claim 15, wherein the X-ray imaging unit further includes a rotational collimator to direct the X-rays at the vehicle, the rotational collimator sharing a common centerline axis with the X-ray tube.

17. The vehicle maintenance system of claim 15, wherein the X-ray tube alignment mechanism includes:
a guide slot to align the X-ray tube into the X-ray imaging system;
a clamp mechanism to clamp the X ray tube being aligned to the X-ray imaging system; and
a safety interlock to indicate a proper alignment of the X-ray tube with the X-ray imaging system.

18. The vehicle maintenance system of claim 15, wherein the one or more rotation mechanisms include:
the roll mechanism to rotate at least the detector array about the roll axis; and
a yaw mechanism to rotate at least the detector array about the yaw axis.

19. The vehicle maintenance system of claim 15, wherein the X-ray imaging unit further includes a mobile container tethered to the X-ray imaging unit, the high voltage power source to the X-ray imaging system stored within the mobile container while the X-ray imaging unit operationally generates the image of the vehicle.

* * * * *